United States Patent
Bolek et al.

(10) Patent No.: US 10,569,367 B2
(45) Date of Patent: Feb. 25, 2020

(54) METHOD TO PREDICT A STRENGTH OF AN ULTRASONIC WELD-JOINT

(71) Applicant: Aptiv Technologies Limited, St. Michael (BB)

(72) Inventors: Katarzyna Bolek, Skawina (PL); Grzegorz Paletko, Zabierzow (PL)

(73) Assignee: Aptiv Technologies Limited (BB)

( * ) Notice: Subject to any disclaimer, the term of this patent is extended or adjusted under 35 U.S.C. 154(b) by 300 days.

(21) Appl. No.: 15/698,907

(22) Filed: Sep. 8, 2017

(65) Prior Publication Data

US 2018/0169795 A1 Jun. 21, 2018

(30) Foreign Application Priority Data

Dec. 15, 2016 (EP) .................................. 16204392

(51) Int. Cl.
*B23K 31/12* (2006.01)
*B23K 20/10* (2006.01)
*G01G 19/414* (2006.01)

(52) U.S. Cl.
CPC ............ *B23K 31/125* (2013.01); *B23K 20/10* (2013.01); *G01G 19/414* (2013.01)

(58) Field of Classification Search
CPC .. G01N 2203/0296; G01N 19/04; G01N 5/04; B23K 20/10; B23K 2101/32; B23K 2101/38; B23K 31/125; G01G 19/414
See application file for complete search history.

(56) References Cited

U.S. PATENT DOCUMENTS

| | | | | |
|---|---|---|---|---|
| 3,192,474 A | * | 6/1965 | Cherry | G01N 3/00 324/693 |
| 3,916,304 A | * | 10/1975 | Roemer | G01N 27/20 324/718 |
| 4,503,392 A | * | 3/1985 | Fastritsky | G01N 27/9046 324/232 |
| 5,412,997 A | * | 5/1995 | Hu | G01N 19/04 73/150 A |
| 5,415,047 A | * | 5/1995 | Maciejewski | G01N 3/04 73/850 |
| 5,587,537 A | * | 12/1996 | Simmons | G01N 3/00 73/862.392 |
| 6,393,924 B1 | * | 5/2002 | Eder | B23K 20/10 73/850 |
| 6,986,288 B2 | * | 1/2006 | Ichikawa | G01N 3/00 73/850 |

(Continued)

*Primary Examiner* — Natalie Huls
(74) *Attorney, Agent, or Firm* — Robert J. Myers

(57) ABSTRACT

A method used to predict a strength of an ultrasonic weld-joint of a wire-cable comprising the steps of providing a wire-cable, determining a combined-weight, removing a contaminant, removing a solvent, determining a weight, determining a percentage by weight of the contaminant, and determining whether the percentage by weight of contaminant is less than a threshold. Determining the percentage by weight of the contaminant removed from the wire-cable is based on a formula [(Mb−Ma)/Mb]*100, where Mb is the combined-weight of the wire-cable and the contaminant and Ma is the weight of the wire-cable. The threshold of the percentage by weight of the contaminant correlates to the strength of the ultrasonic weld-joint.

10 Claims, 4 Drawing Sheets

(56) References Cited

U.S. PATENT DOCUMENTS

| | | | |
|---|---|---|---|
| 8,549,928 B2* | 10/2013 | Langlais | G01N 3/20 73/150 A |
| 2018/0172570 A1* | 6/2018 | Bolek | G01N 1/44 |
| 2019/0271669 A1* | 9/2019 | Suter | G01N 29/12 |

* cited by examiner

METHOD TO PREDICT A STRENGTH OF AN ULTRASONIC WELD-JOINT

CROSS-REFERENCE TO RELATED APPLICATION

This application claims the benefit under 35 U.S.C. § 119(a) of European Patent Application 16204392.1, filed Dec. 15, 2016, the entire disclosure of which is hereby incorporated herein by reference.

TECHNICAL FIELD OF INVENTION

This disclosure generally relates to an ultrasonic weld-joint, and more particularly relates to a method to predict a strength of the ultrasonic weld-joint.

BACKGROUND OF INVENTION

It is known that excess contamination on the surface of aluminum and copper wire-cable may negatively impact the strength of an ultrasonic weld-joint. International standards only provide a qualitative specification for cleanliness to be consistent with the best commercial practices and to not impair utilization.

SUMMARY OF THE INVENTION

In accordance with one embodiment, a method used to predict a strength of an ultrasonic weld-joint of a wire-cable is provided. The method is comprised of the steps of providing a wire-cable, determining a combined-weight, removing a contaminant, removing a solvent, determining a weight, determining a percentage-by-weight of the contaminant, and determining whether the percentage-by-weight of contaminant is less than a threshold. The step of providing a wire-cable may include providing a sample of a wire-cable containing an organic contaminant. The step of determining a combined-weight may include determining a combined-weight of the wire-cable and the contaminant. The step of removing a contaminant may include removing the contaminant from a surface of the wire-cable using a solvent. The step of removing a solvent may include removing the solvent from the surface of the wire-cable. The step of determining a weight may include determining a weight of the wire-cable. The step of determining a percentage-by-weight of the contaminant may include determining a percentage-by-weight of the contaminant removed from the wire-cable based on a formula $[(Mb-Ma)/Mb]*100$, wherein Mb is the combined-weight of the wire-cable and the contaminant and Ma is the weight of the wire-cable. The step of determining whether the percentage-by-weight of the contaminant is less than a threshold may include determining whether the percentage-by-weight of the contaminant is less than a predetermined threshold, wherein said threshold correlates to the strength of the ultrasonic weld-joint.

Further features and advantages will appear more clearly on a reading of the following detailed description of the preferred embodiment, which is given by way of non-limiting example only and with reference to the accompanying drawings.

BRIEF DESCRIPTION OF DRAWINGS

The present invention will now be described, by way of example with reference to the accompanying drawings, in which.

DETAILED DESCRIPTION

Figure 1A:
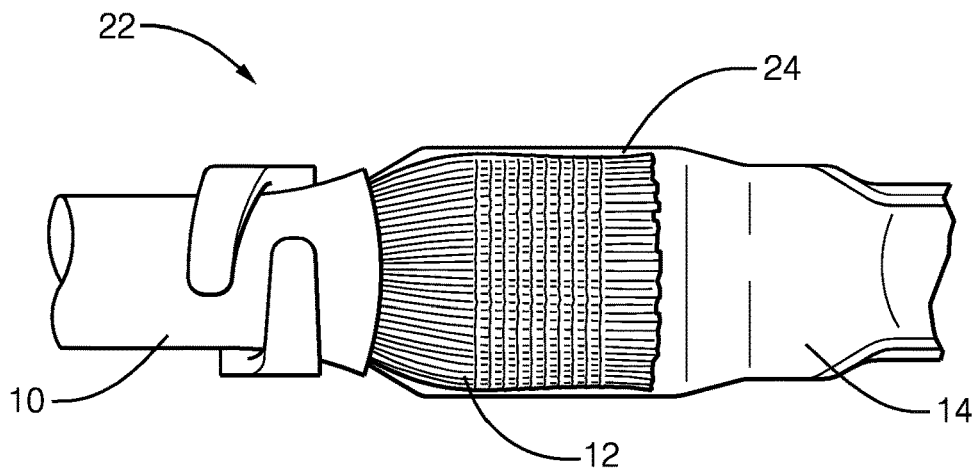
FIG. 1A is a top-view of an ultrasonic weld-joint in accordance with one embodiment.

Ultrasonic welding (USW) is a known process for terminating a wire-cable 10. Wire-cable 10, and typically a stranded-wire-core 12, is used for automotive applications including, but not limited to, battery-cables, for example. USW imparts a high-frequency vibration into the wire-cable 10 and into a mating terminal 14, which are held together by a clamping-force, to generate friction between the external surface 16 of the wire-cable 10 and the terminal 14. The friction creates a sufficiently high temperature to metallurgically bond the wire-cable 10 and the terminal 14 together without creating a pool of molten metal. A contaminant 18, such as a vanishing oil or other organic compound typically used in the process of wire manufacturing, may negatively affect a strength 20 of an ultrasonic weld-joint 22, hereafter referred to as the weld-joint 22, if the contaminant 18 is present on the surface 16 of the wire-cable 10 in sufficiently large amounts. The invention described herein quantifies a threshold 24 of the contaminant 18 that may predict the strength 20 of the weld-joint 22.

The wire-cable 10 may be formed from an aluminum-based material 26 or a copper-based material 28, both of which may be plated with a conductive material including, but not limited to, tin 30.

Figure 1B:
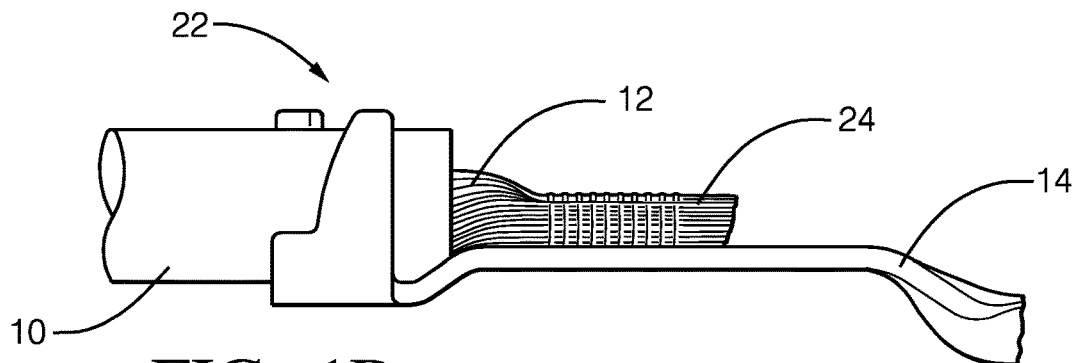
FIG. 1B is a side-view of the ultrasonic weld-joint of FIG. 1A in accordance with one embodiment.

FIG. 1A illustrates a non-limiting example of a top-view of the weld-joint 22 where the stranded-wire-core 12 is welded to the terminal 14. FIG. 1B illustrates a non-limiting example of a side-view of the weld-joint 22 of FIG. 1A where the stranded-wire-core 12 is welded to the terminal 14. Note that a cut-end 32 of the stranded-wire-core 12 is deformed due to the USW process, as will be recognized by one skilled in the art.

Figure 2:
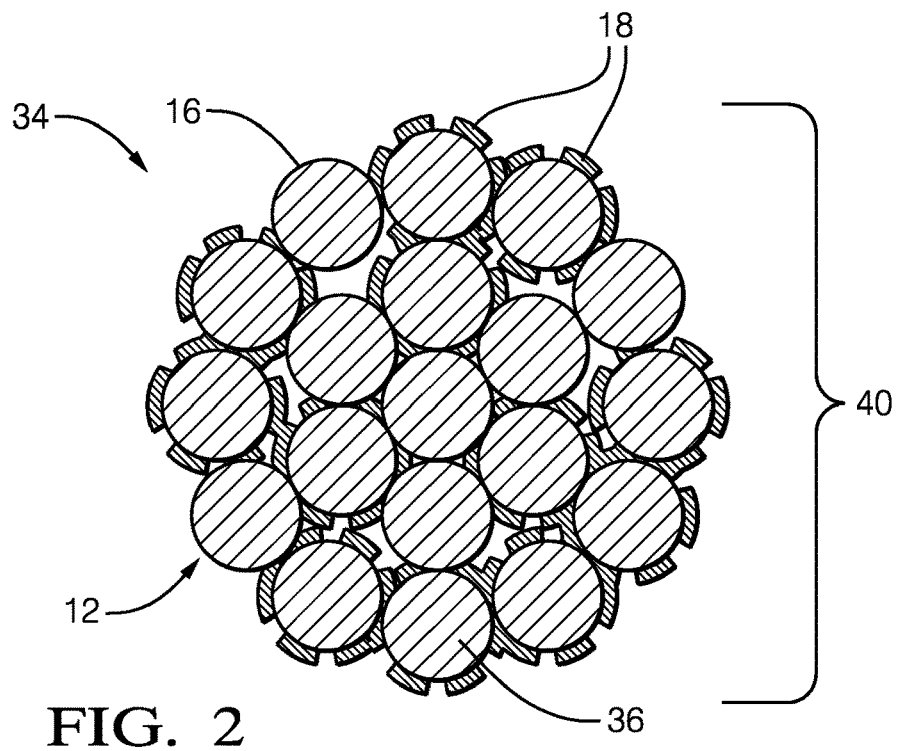
FIG. 2 is a cross-section view of a stranded-wire-core in accordance with one embodiment.

FIG. 2 illustrates a non-limiting example of a cross-section 34 of the stranded-wire-core 12 containing the contaminant 18 on the surface 16 of the individual wire-strands 36. The contaminant 18 may be a vanishing oil or other organic compound that may be used as a lubricant during the wire manufacturing process.

Figure 3:
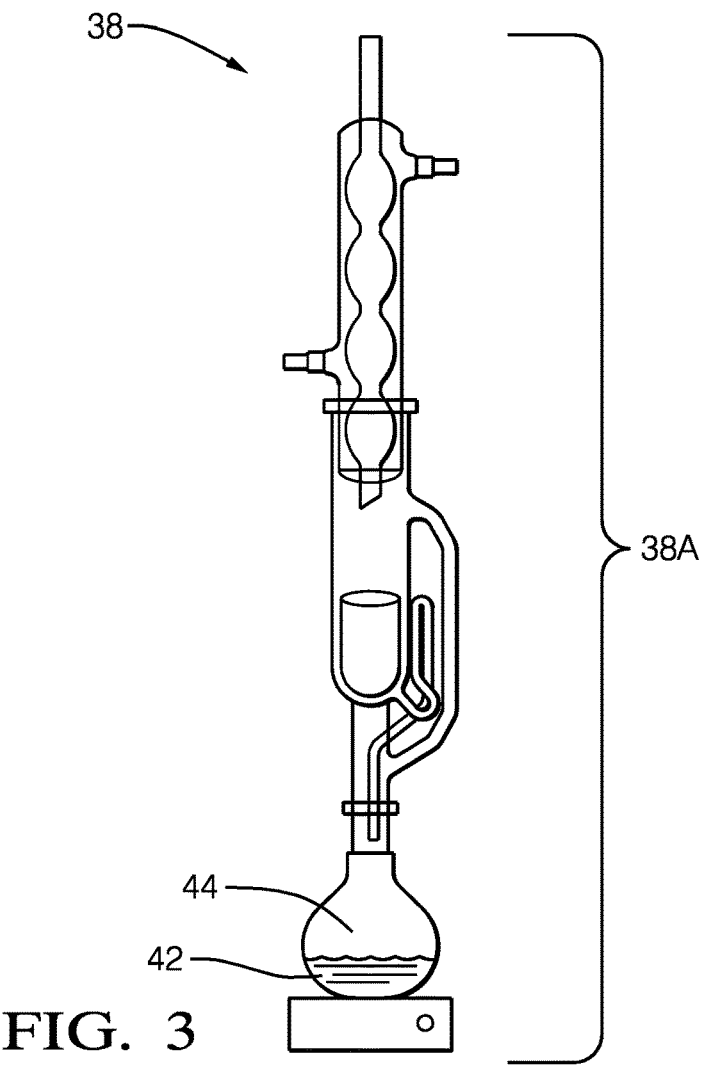
FIG. 3 is an illustration of a cleaning apparatus in accordance with one embodiment.

FIG. 3 illustrates a cleaning apparatus 38, such as a Soxhlet extractor 38A, that may be used to remove the contaminant 18 from the surface 16 of the wire-cable 10. A sample of the wire-cable 10 containing the contaminant 18 is weighed using a scale, after removing any insulation, to determine a combined-weight 40 (FIG. 2) of the wire-cable 10 and the contaminant 18 prior to removing the contaminant 18 from the wire-cable 10. The sample of the wire-cable 10 may be placed inside the cleaning apparatus 38 and the sample is rinsed by a solvent 42 that is heating to a boiling-point 44 of the solvent 42 causing the solvent 42 to reflux, as will be recognized by one skilled in the art. Multiple reflux cycles may be performed to ensure the removal of the contaminant 18. Experimentation by the inventors has found that five (5) reflux cycles are sufficient to remove the contaminant 18 from the wire-cable 10. The solvent 42 used in the cleaning apparatus 38 may be any solvent 42 compatible with the materials of the wire-cable 10 and may include diethyl ether 46, trichloromethane 48, and 2-propanone 50. Other solvents 42 that may be used are envisioned, but not listed.

Upon removal of the contaminant 18 from the wire-cable 10, the solvent 42 is removed from the surface 16 of the wire-cable 10 by placing the wire-cable 10 in a desiccator-device 52, such as a desiccator that contains a desiccant, as will be recognized by one skilled in the art. Experimentation by the inventors has found that the wire-cable 10 should remain in the desiccator-device 52 for a minimum of twelve-hours (12-hours) at a temperature of between 15° C. and 30° C. and at a pressure of between 50 kilopascal (kPa) and 150 kPa. The wire-cable 10 is then weighed using the scale to determine a weight 54 of the wire-cable 10 without the contaminant 18, as illustrated in FIG. 4.

Figure 4:
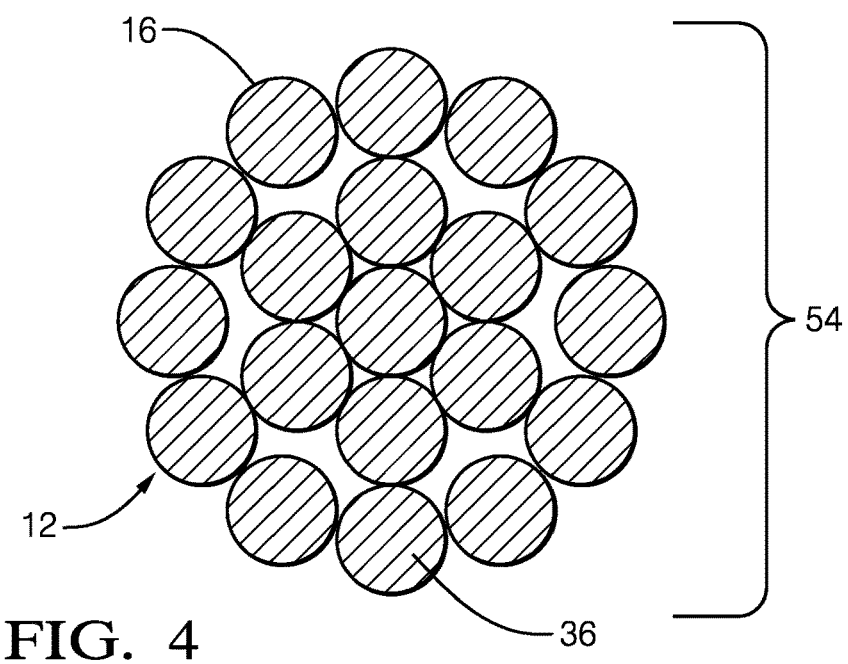
FIG. 4 is a cross-section view of the stranded-wire-core in accordance with one embodiment.

A percentage-by-weight 56 of the contaminant 18 removed from the wire-cable 10 may be determined based on a formula $[(Mb-Ma)/Mb]*100$, where Mb is defined as the combined-weight 40 of the wire-cable 10 and the contaminant 18 (FIG. 2), and Ma is defined as the weight 54 of the wire-cable 10 with the contaminant 18 removed (FIG. 4).

Figure 5:
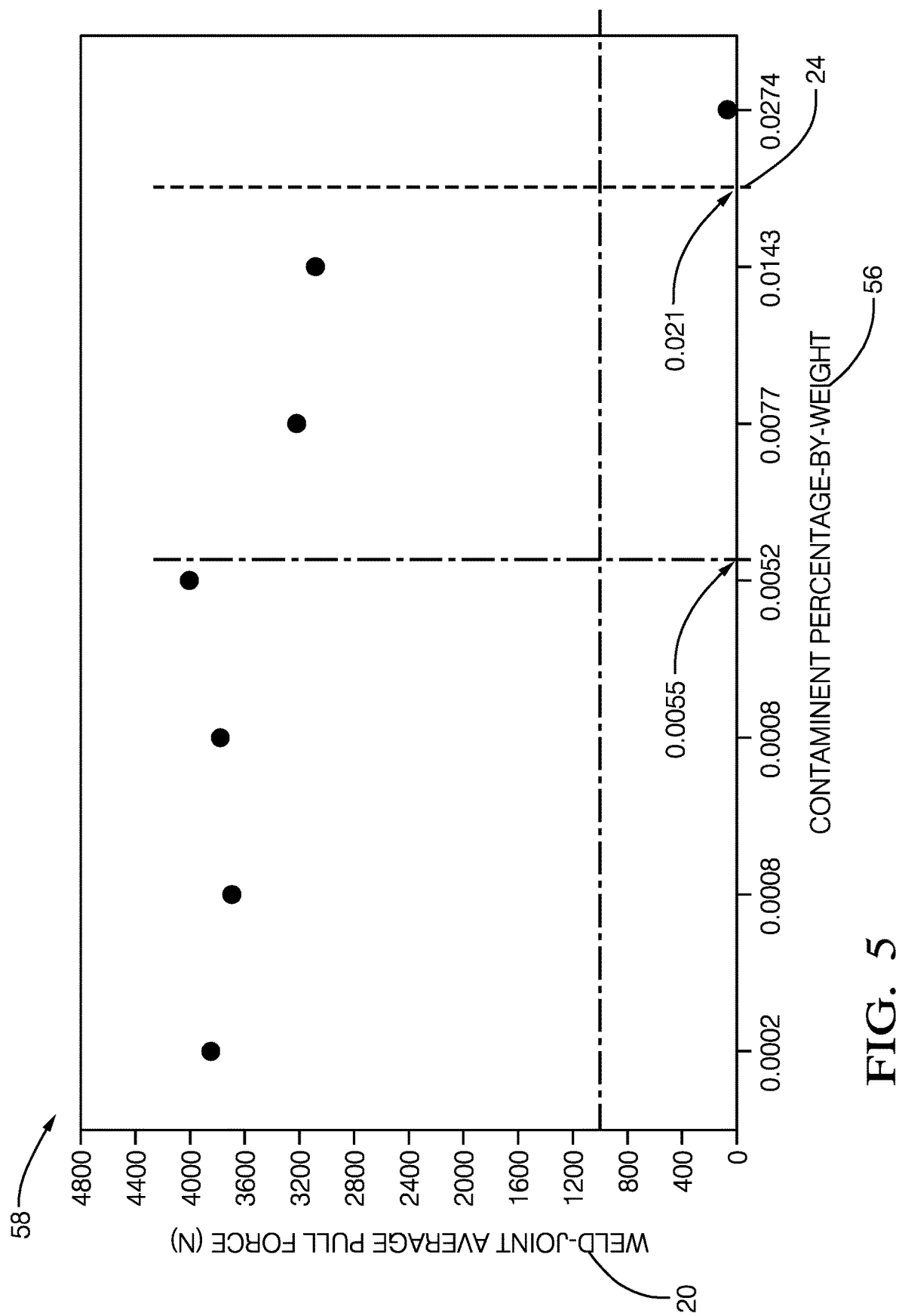
FIG. 5 is a graph of a strength of the weld-joint relative to a percentage of contamination of a wire by weight in accordance with one embodiment.

FIG. 5 is a graph 58 that illustrates a relationship between the percentage-by-weight 56 of the contaminant 18 removed from the wire-cable 10 and the strength 20 of the weld-joint 22. Experimentation by the inventors has found that there is a correlation between the percentage-by-weight 56 of contaminant 18 on the wire-cable 10 that is ultrasonically welded and the strength 20 of the weld-joint 22. The strength 20 of the weld-joint 22 may be characterized by a pull-force. The pull-force is defined as the tensile-force required to separate the bond between the wire-cable 10 and the terminal 14. Other metrics used to characterize the strength 20 of the weld-joint 22 are contemplated, but not shown, and will be apparent to one skilled in the art. Experimentation by the inventors has found that the pull-force of greater than 1200 Newtons (1200 N) is sufficient to provide a durable weld-joint 22. FIG. 5 also illustrates the threshold 24 of the percentage-by-weight 56 of the contaminant 18 removed from the wire-cable 10, below which is determined to provide a weld-joint 22 of sufficient strength 20 to be applicable for automotive applications. In addition, the threshold 24 is set sufficiently low to provide for a controllable USW process. As illustrated in FIG. 5 the inventors have discovered that a significant reduction in strength 20 occurs when the percentage-by-weight 56 of the contaminant 18 is increased above 0.0143%. By assuming a linear relationship between the strength 20 and the percentage-by-weight 56 for this range of values, a threshold 24 of less than 0.021% may be indicative of a durable weld-joint 22. The threshold 24 may be further reduced to less than 0.0055% to further increase the strength 20 of the weld-joint 22, as also indicated in FIG. 5.

Figure 6:
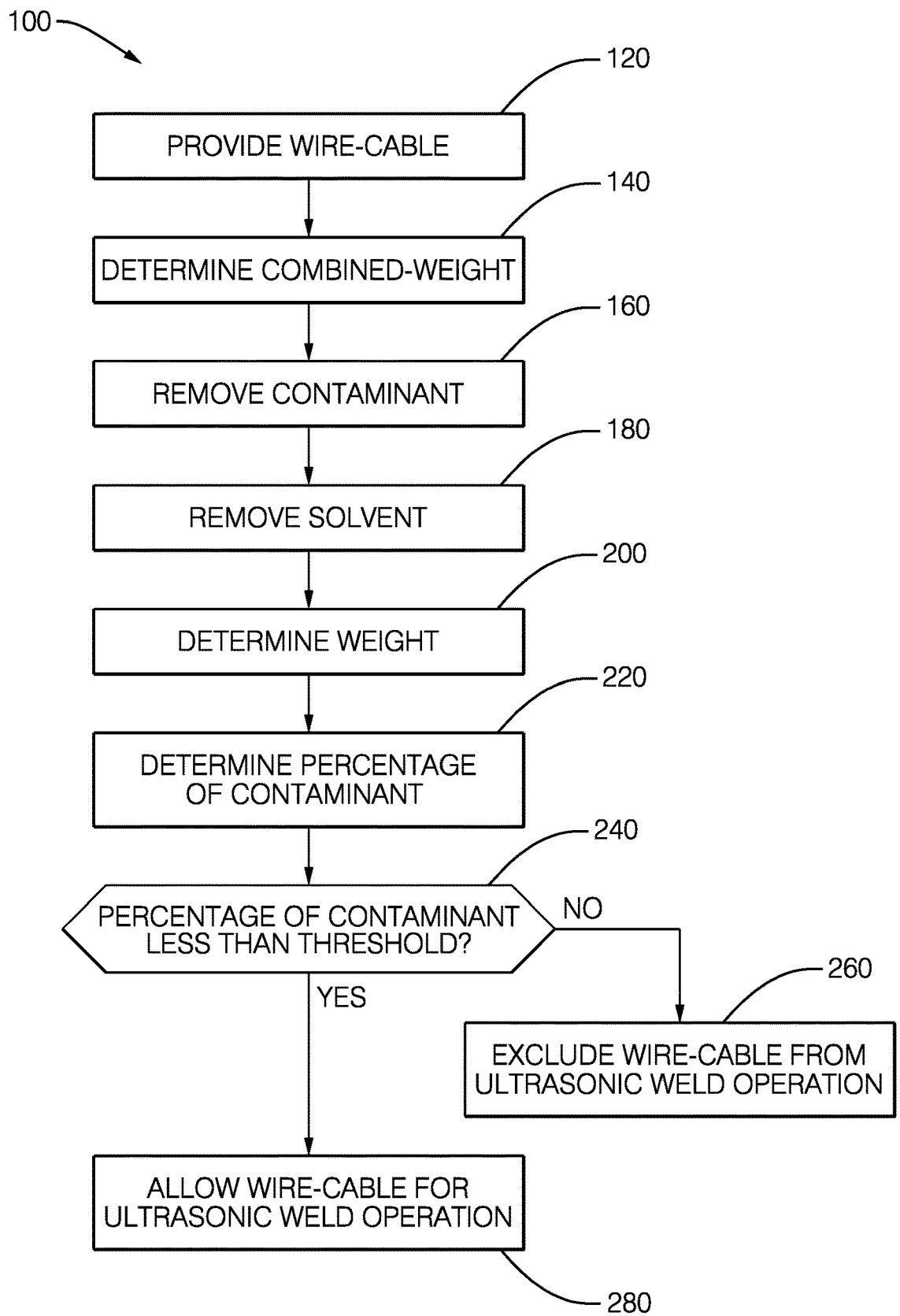
FIG. 6 is a flow chart of a method of predicting the strength of the weld-joint in accordance with one embodiment.

FIG. 6 illustrates a non-limiting example of a method 100 used to predict the strength 20 of the ultrasonic weld-joint 22 of the wire-cable 10.

Step 120, PROVIDE WIRE-CABLE, may include the step of providing the sample of the wire-cable 10 containing the organic contaminant 18. A length of wire-cable 10 is cut from a spool and any insulation is removed from the wire-cable 10 prior to placing the sample on the scale. Experimentation by the inventors has found that the length of wire-cable 10 with a corresponding mass of between 50 grams (50 g) to 310 g provides a detectable amount of the contaminant 18.

Step 140, DETERMINE COMBINED-WEIGHT, may include the step of determining the combined-weight 40 of the sample of wire-cable 10 and the contaminant 18 by weighing the sample using the scale. Any scale, and preferably an analytical balance, with a capacity sufficient for the mass of the sample and a resolution of 0.1 milligrams (0.1 mg) may be used, such as the Model AS 310.R2 Manufactured by RADWAG Balances and Scales of Radom, Poland.

Step 160, REMOVE CONTAMINANT, may include the step of removing the contaminant 18 from the surface 16 of the wire-cable 10 using the solvent 42.

Step 180, REMOVE SOLVENT, may include the step of removing the solvent 42 from the surface 16 of the wire-cable 10.

Step 200, DETERMINE WEIGHT, may include the step of determining the weight 54 of the wire-cable 10 with the contaminant 18 removed and the solvent 42 removed.

Step 220, DETERMINE PERCENTAGE OF CONTAMINANT, may include the step of determining the percentage-by-weight 56 of the contaminant 18 removed from the wire-cable 10 based on the formula $[(Mb-Ma)/Mb]*100$, wherein Mb is the combined-weight 40 of the wire-cable 10 and the contaminant 18 and Ma is the weight 54 of the wire-cable 10.

Step 240, DETERMINE IF PERCENTAGE OF CONTAMINANT LESS THAN THRESHOLD, may include the step of determining whether the percentage-by-weight 56 of the contaminant 18 is less than the predetermined threshold 24, wherein the threshold 24 correlates to the strength 20 of the ultrasonic weld-joint 22.

Step 260, EXCLUDE WIRE-CABLE FROM ULTRASONIC WELD OPERATION, may include the step of excluding a batch of the wire-cable 10 from the USW process if the percentage-by-weight 56 of the contaminant 18 is not less than the predetermined threshold 24.

Step 280, ALLOW WIRE-CABLE FOR ULTRASONIC WELD OPERATION, may include the step of allowing a batch of wire-cable 10 to the USW process if the percentage-by-weight 56 of the contaminant 18 is less than the predetermined threshold 24.

Accordingly, a method 100 used to predict the strength 20 of the ultrasonic weld-joint 22 of a wire-cable 10 is provided. Experimentation by the inventors has found that there is a correlation between the percentage-by-weight 56 of the contaminant 18 on the wire-cable 10 that is ultrasonically welded, and the strength 20 of the weld-joint 22. The level of the threshold 24 of the percentage-by-weight 56 of the contaminant 18 also impacts the stability of the USW process.

While this invention has been described in terms of the preferred embodiments thereof, it is not intended to be so limited, but rather only to the extent set forth in the claims that follow. Moreover, the use of the terms first, second, upper, lower, etc. does not denote any order of importance, location, or orientation, but rather the terms first, second, etc. are used to distinguish one element from another. Furthermore, the use of the terms a, an, etc. do not denote a limitation of quantity, but rather denote the presence of at least one of the referenced items.

We claim:

1. A method used to predict a strength of an ultrasonic weld-joint of a wire-cable, comprising the steps of:

providing a sample of a wire-cable containing an organic contaminant;
determining a combined-weight of the wire-cable and the contaminant;
removing the contaminant from a surface of the wire-cable using a solvent;
removing the solvent from the surface of the wire-cable;
determining a weight of the wire-cable;
determining a percentage-by-weight of the contaminant removed from the wire-cable based on a formula $[(M_b-M_a)/M_b]*100$, wherein $M_b$ is the combined-weight of the wire-cable and the contaminant and $M_a$ is the weight of the wire-cable; and
determining whether the percentage by weight of the contaminant is less than a predetermined threshold, wherein said threshold correlates to the strength (20) of the ultrasonic weld-joint.

2. The method in accordance with claim 1, wherein the wire-cable is a stranded-wire-core.

3. The method in accordance with claim 1, wherein the wire-cable is formed from material selected from the list consisting of aluminum-based material and copper-based material.

4. The method in accordance with claim 3, wherein the wire-cable is plated with tin.

5. The method in accordance with claim 1, wherein the solvent is selected from the list consisting of diethyl ether, trichloromethane, and 2-propanone.

6. The method in accordance with claim 1, further comprising the step of heating the solvent to a boiling-point.

7. The method in accordance with claim 1, further comprising the steps of:
placing the sample within a Soxhlet extractor; and
rinsing the sample with the solvent within the Soxhlet extractor.

8. The method in accordance with claim 1, wherein the step of removing the solvent from the surface of the wire-cable is performed using a desiccator-device.

9. The method in accordance with claim 8, wherein the wire-cable is held in the desiccator-device for greater than twelve hours.

10. The method in accordance with claim 1, wherein said threshold is 0.021 percentage-by-weight.

\* \* \* \* \*